United States Patent
Wagner

[11] Patent Number: 6,047,711
[45] Date of Patent: Apr. 11, 2000

[54] METHOD AND APPARATUS FOR CONVERTING A POWER-DRIVEN TOOTHBRUSH INTO A POWER-DRIVEN FLOSSING DEVICE

[76] Inventor: Daniel A. Wagner, 2784 Wimbledon Dr., Aptos, Calif. 95003

[21] Appl. No.: 09/253,256

[22] Filed: Feb. 19, 1999

[51] Int. Cl.[7] .................................................. A61C 15/00
[52] U.S. Cl. ........................................ 132/322; 132/323
[58] Field of Search ................................. 132/322, 323, 132/324, 325, 309, 311, 321; 433/118, 119, 122, 123; 128/62 A; 15/22.1

[56] References Cited

U.S. PATENT DOCUMENTS

| | | | |
|---|---|---|---|
| Re. 35,712 | 1/1998 | Murayama | 132/322 |
| 3,822,432 | 7/1974 | Skinner . | |
| 4,019,522 | 4/1977 | Elbreder . | |
| 4,178,947 | 12/1979 | McCourry et al. . | |
| 4,235,253 | 11/1980 | Moore . | |
| 4,245,658 | 1/1981 | Lecouturier | 132/92 A |
| 4,377,877 | 3/1983 | O'Rourke . | |
| 4,817,642 | 4/1989 | Lipp . | |
| 4,830,032 | 5/1989 | Jousson . | |
| 4,880,382 | 11/1989 | Moret et al. | 433/118 |
| 5,010,906 | 4/1991 | Preciutti . | |
| 5,033,150 | 7/1991 | Gross et al. | 15/22.1 |
| 5,085,236 | 2/1992 | Odneal et al. | 132/325 |
| 5,086,792 | 2/1992 | Chodorow . | |
| 5,104,315 | 4/1992 | McKinley . | |
| 5,142,723 | 9/1992 | Lustic et al. . | |
| 5,170,809 | 12/1992 | Imai et al. | 132/322 |
| 5,183,065 | 2/1993 | Mason . | |
| 5,184,632 | 2/1993 | Gross et al. . | |
| 5,189,751 | 3/1993 | Giuliani et al. . | |
| 5,263,218 | 11/1993 | Giuliani et al. . | |
| 5,305,492 | 4/1994 | Giuliani et al. . | |
| 5,309,590 | 5/1994 | Giuliani et al. . | |
| 5,373,153 | 12/1994 | Cumberledge et al. . | |
| 5,378,153 | 1/1995 | Giuliani et al. . | |
| 5,476,384 | 12/1995 | Giuliani et al. . | |
| 5,483,982 | 1/1996 | Bennett et al. . | |
| 5,545,480 | 8/1996 | Lalani | 132/321 |
| 5,573,020 | 11/1996 | Robinson . | |
| 5,638,841 | 6/1997 | Levine . | |
| 5,662,130 | 9/1997 | Wiltshire . | |
| 5,680,876 | 10/1997 | Hasham et al. | 132/320 |
| 5,699,575 | 12/1997 | Pelfer . | |
| 5,709,233 | 1/1998 | Boland et al. . | |
| 5,718,667 | 2/1998 | Sugimoto et al. | 132/322 |
| 5,722,440 | 3/1998 | Urso . | |
| 5,749,380 | 5/1998 | Zebuhr . | |
| 5,762,078 | 6/1998 | Zebuhr | 132/322 |
| 5,784,742 | 7/1998 | Giuliani et al. . | |
| 5,796,325 | 8/1998 | Lundell et al. . | |
| 5,815,872 | 10/1998 | Meginniss, III et al. . | |
| 5,829,458 | 11/1998 | Chodorow | 132/323 |
| 5,875,797 | 3/1999 | Chiang et al. | 132/321 |
| 5,906,213 | 5/1999 | Diffendal . | |

OTHER PUBLICATIONS

Three–page document entitled *Interplak®* Power Flosser Attachment, authored by Conair Corporation and dated Nov., 1998, and available from Conair Corporation, 7475 N. Glen Harbor Blvd., Glandale, AZ 85307.

*Primary Examiner*—Gene Mancene
*Assistant Examiner*—Pedro Philogene
*Attorney, Agent, or Firm*—C. Michael Zimmerman

[57] ABSTRACT

A converter is described for converting a power-driven toothbrush into a power-driven flossing device. Such converter includes a yoke for holding floss string and an arrangement for receiving energy from a toothbrush originally provided to move toothbrush bristles and convert such energy into movement of a floss string.

6 Claims, 2 Drawing Sheets

METHOD AND APPARATUS FOR CONVERTING A POWER-DRIVEN TOOTHBRUSH INTO A POWER-DRIVEN FLOSSING DEVICE

CROSS-REFERENCES TO RELATED DOCUMENTS

This patent application is based at least partly on Disclosure Document No. S00800 filed Jul. 7, 1998.

BACKGROUND OF THE INVENTION

This present invention relates to dental hygiene and, more particularly, to a method of converting a power-driven toothbrush into a power-driven flossing device, and a converter especially adapted to facilitate such conversion.

Most people in industrial societies are devoting meaningful attention to dental hygiene. The brushing of teeth is considered to be basic to dental hygiene, and power-driven toothbrushes are common although many consider them relatively expensive.

The art of power-driven toothbrushes is well established. It is not unusual for one who brushes his/her teeth with a power-driven toothbrush to become interested at a later time in using tooth flossing to supplement the brushing. That is, in many situations it is after a consumer purchases a power-driven toothbrush that he/she becomes interested in also flossing. If such a person uses a power-driven toothbrush, the person is relegated to flossing by hand to avoid the expense of also purchasing a power-driven flossing device.

As mentioned previously, the art of power-driven toothbrushes is well established. There also are, of course, power-driven flossing devices. Some have even designed power-driven toothbrush/flossing device combinations. However, as also mentioned previously it is not unusual for someone to become interested in flossing after purchasing a relatively expensive power-driven toothbrush. These combination units are therefore considered by many to be a compromise by those interested primarily in tooth brushing and therefore are not widely accepted.

Some of the patents which were considered before the filing of this patent application include U.S. Pat. Nos. RE 35712; 4,014,354; 4,235,253; 4,377,877; 4,605,025; 4,817,642; 4,830,032; 5,010,906; 5,189,751; 5,261,430; 5,263,218; 5,267,579; 5,305,492; 5,309,590; 5,343,873; 5,373,153; 5,375,615; 5,378,153; 5,476,384; 5,544,382; 5,636,988; 5,749,380; 5,762,078; 5,784,742; 5,796,325; and 5,815,872; Review was also made of International Patent WO 90/11057 and WO 94/15546. None of these patents was found to either anticipate or make obvious applicant's solution to the problem of a person who has invested in a power-driven toothbrush at a later time also wishing he/she had a power-driven low-cost but effective flossing device. And none show the details of applicant's arrangement.

U.S. Pat. No. 5,085,236 (Odneal et al.) discloses a flossing attachment for an electric toothbrush. However, it appears the inventors only went half-way. That is, while the attachment is designed to be "attached" to an electric toothbrush, there is no disclosure in such patent regarding the diversion of energy from the toothbrush to move the floss string. Moreover, this arrangement lacks simplicity and may endanger proper dental hygiene by storing used floss string in close proximity to the supply of new string. Such storage gives removed bacteria the opportunity to multiply and return into a user's mouth during subsequent uses.

SUMMARY OF THE INVENTION

The present invention enables effective power-driven flossing for those who undergo the expense of obtaining a power-driven toothbrush before making the decision to also floss. The method of the invention accomplishes this by configuring a flossing device to harness the energy of an existing power-driven toothbrush to also provide flossing. A user is therefore able to obtain power-driven flossing without undergoing the expense of obtaining a power-driven flosser after the expense of obtaining a power-driven toothbrush. In this connection, the method includes the step after an electric power-driven toothbrush is provided, of configuring a flossing device to receive energy from the toothbrush and convert the same into movement of floss string.

The invention includes a converter which is especially designed to carry out the method. It includes means for receiving all or part of the energy originally provided in a power-driven toothbrush to move toothbrush bristles, and then converting the same into movement of a floss string.

The device includes the typical yoke found in many flossing devices, and as an important addition one or more of the yoke arms may be provided with a cavity or pocket for receiving a flowable flossing compound which will interact with the floss string during a flossing operation. Most desirably each of the arms has a cavity, and each cavity includes both a compound holding portion and a metering portion to regulate the flow of the flossing compound towards the floss string. It is to be noted that while the provision of flowable flossing compound cavities in the yoke combines with the other features of the invention to provide an enhanced flossing operation, such feature is usable on other, non-powered flossing devices.

The arm ends of the yoke are further configured to interact as will be described, with an anomaly such as a bead, provided in a floss string. It also includes a floss string which may be made up of a number of filaments, at least one of which is provided with a flossing component and, as will be explained below, is most desirably covered with other filaments to assure that the cleansing action initiated by the same only is effective at the flossed tooth or teeth.

It will be recognized that because of the nature of the flossing device, i.e., the fact that it is designed after a power-driven toothbrush is designed for its purpose, various embodiments of such flossing device are necessary to cover the range of power-driven toothbrushes which are dominant in the market. Other features and advantages of the invention either will become apparent or will be described in connection with the following, more detailed description of preferred embodiments of the invention and variations.

BRIEF DESCRIPTION OF THE DRAWINGS

With reference to the accompanying drawings.

DETAILED DESCRIPTION OF THE PREFERRED EMBODIMENTS

The following, relatively detailed description is provided to satisfy the patent statutes. It will be appreciated by those skilled in the art, though, that various changes and modifications can be made without departing from the invention.

Figure 1:
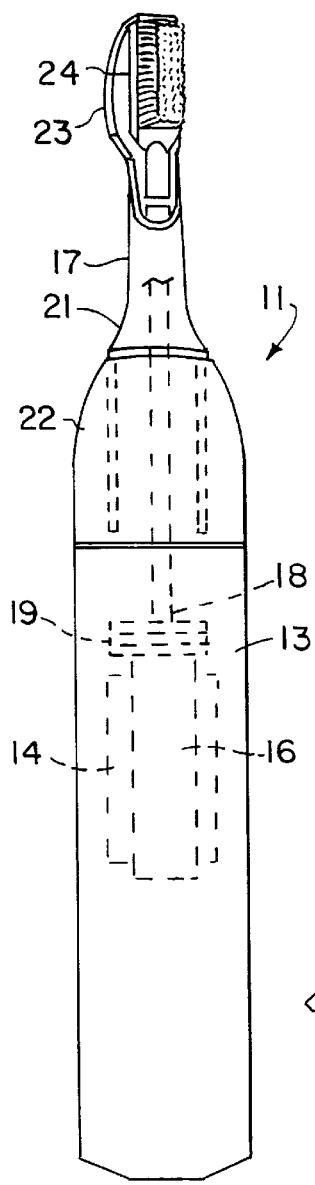
FIG. 1 is a side elevation view of a typical power-driven toothbrush.

A standard power-driven toothbrush is generally indicated by the reference numeral 11 in FIG. 1. Such toothbrush includes a handle/electronics/battery assembly 13. This assembly provides one of a pair of drive components for operating the bristles of the toothbrush. In this embodiment, the "handle" drive component includes an electromagnet schematically represented at 14 surrounding an iron core 16.

The toothbrush portion is provided as a head, generally referred to by the reference numeral 17. Such head includes a second drive component 18 having a permanent magnet arrangement 19 held in position in the handle assembly 13 to receive driving energy from the electromagnet 14. The head driving component is surrounded by inner 21 and outer 22 couplings. The outer coupling is threadably received (not shown) on an end of the handle 13 and holds the drive component 18 in a position projecting into such handle. The inner coupling is provided to facilitate such coupling and protrudes beyond the outer coupling to form a shell 23 to protect the toothbrush bristles and their mount 24.

Figure 2:
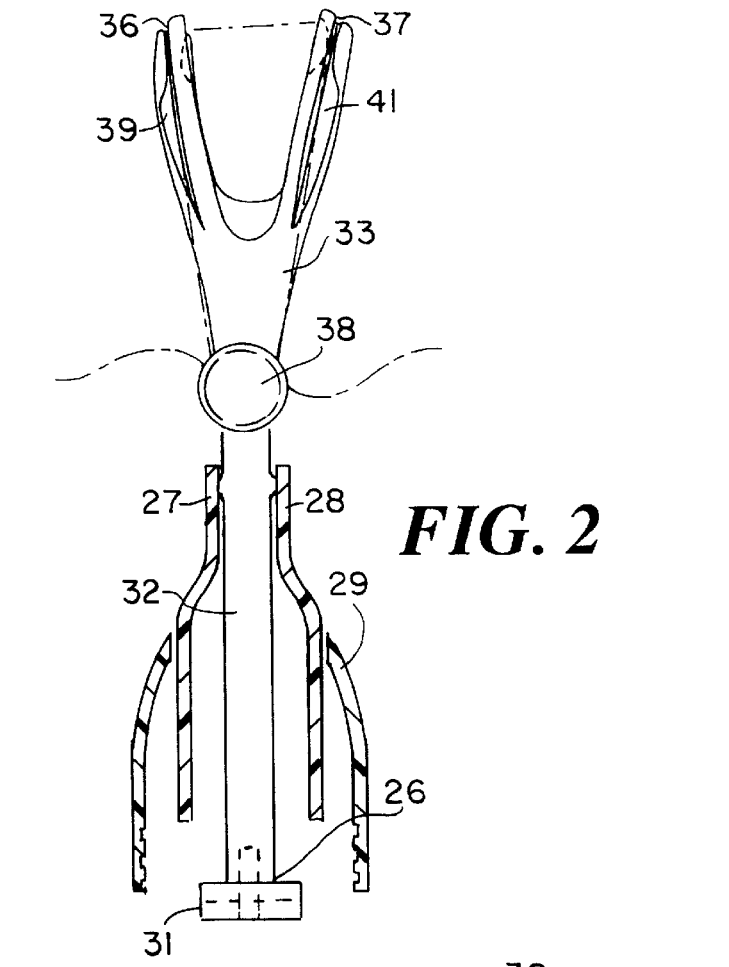
FIG. 2 is a side elevation view with a portion broken away of a preferred embodiment of a tooth flossing converter of the invention.
Figure 3:
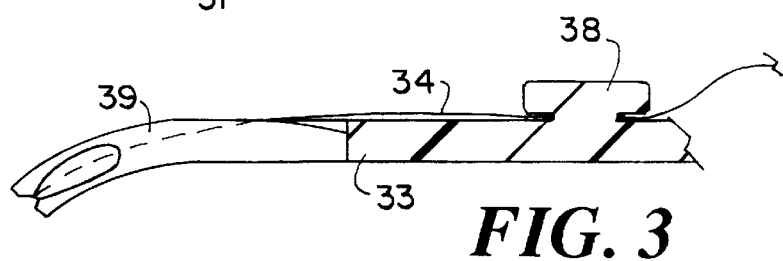
FIG. 3 is a side sectional view of the yoke of the preferred embodiment of FIG. 2.

A preferred embodiment of a flossing converter of the invention, designed to operate with the toothbrush handle assembly 13, is illustrated in FIG. 2. Such connector includes a drive component 26 which is designed to take the place of toothbrush drive component 18. The drive component 26 receives vibratory motion from the handle assembly and, in this connection, the converter is provided with pivot protrusions 27 which engage an inner coupling 28 as illustrated. The flossing device is similar to the toothbrush head in that it includes both the inner coupling 28 and an outer coupling 29. It is important to note that during operation of the driving component, the couplings are stationary and protect a user from the vibration associated with the driving components. The outer lower free end of the coupling is threaded internally to enable the device both to be attached to, and subsequently removed from, a toothbrush handle assembly 13.

The inner and outer coupling devices cooperate to hold the device not only on the handle but also to hold it in such a position that permanent magnets 31 provided on the end of drive component 26 are positioned to receive energy from the handle assembly 13. Thus, the permanent magnets act as means for receiving energy from the toothbrush originally provided to move toothbrush bristles. Once received, this energy is used for movement (in this case vibratory movement) of floss string represented at 34 rather than movement of brush bristles. Such movement is transmitted via a shaft 32 to a yoke 33 to the floss string held taut between two yoke arm ends 36 and 37. If desired, a flexible, resilient or other frequency absorbing coupling can be provided between the yoke and the drive component 26 to reduce or otherwise tailor the energy received from such drive component before it is transmitted to the yoke.

The common area of the yoke 33 includes a tie-in post 38 for the floss string. The floss string is wrapped around the tie-in post 38; threaded up the exterior of the yoke arm providing arm end 36 through a groove 39; is passed through the space between the arm ends; and is brought down again to the tie-in post 38 through a groove 41 provided on the exterior of the yoke arm having end 37.

Figure 4:
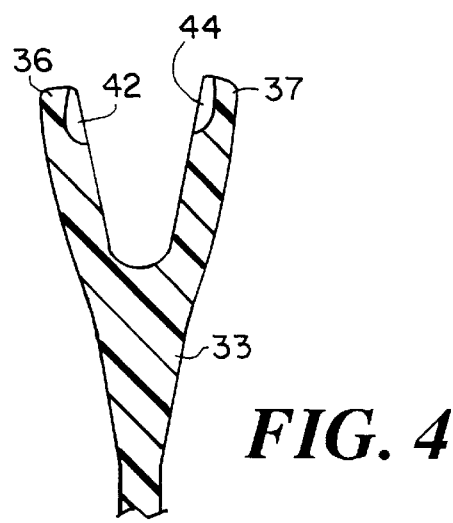
FIG. 4 is an enlarged sectional view showing details of the yoke of the preferred embodiment of FIG. 2.

As an added feature of the invention, small cavities are provided in the immediate vicinity of the free arm ends to enable small quantities of a compound useful to dental hygiene to be added to the taut dental flossing string during the flossing process. That is, as shown a first floss compound bearing cavity 42 is provided on the interior side of arm end 36 and a second flossing compound bearing cavity 44 is provided on the interior side of arm end 37. (These cavities are best illustrated in FIG. 4.) By providing two cavities and filling cavity 42 with a flossing compound that reacts to cause effervescence, or some other useful reaction deemed beneficial to the cleaning process when mixed with the contents of the second cavity 44, an improved cleaning process is provided. The two flossing compounds seep on the flossing string to mix in the general area of the middle of the suspended length of floss string which is at the time placed in the intra-dental space requiring cleaning. The result of the reaction causes, for example, the abundant discharge of a reaction gas in an effervescence process. The mechanical action of gas movement combined with the liquids present will cause a foam capable of transporting away debris dislocated by the action of the flossing string. By designing the chemical structure of the discharged gas to contain a chemically active component like, for example, oxygen, chlorine, fluorine, or similar, a further active disinfectant and whitening process can be promoted. Yet further benefits to oral hygiene are to be achieved by designing the chemical structure of the discharged gas to contain a biologically active component like, for example, a fungicide, germicide, disinfectant, or similar. Such process has the further benefit of being precisely localized in the intra-dental area and at the tooth-gum interface.

To maximize the localization of the process described here, the two flossing components discussed can be further designed to react in the described way only in the presence of a specialized catalyst. By including the specialized catalyst as a component of the floss string, the expected reaction takes place only in the immediate vicinity of the floss string and only when both flossing compounds are present. Under such circumstances, the simple unintended mixing of the flossing compounds in the mouth has no effect. By making the above described reaction dependent on the presence of the dental floss catalyst, the effect described also can be achieved with a single flossing compound designed to react to the catalyst present on the string of the dental floss. While this embodiment shows two flossing compound bearing cavities, it should be noted that a single flossing compound bearing cavity would be sufficient to provide the useful effect described above.

While the dispensing of one or more flossing compounds to the dental floss during the flossing process is greatly facilitated when powered flossing means are being used, users that prefer to use manual flossing methods can also benefit from the advantages of the process described. In one example, a user holds a string of dental floss taut between the fingers of two hands while holding a dispensing container in at least one hand. By gently squeezing the dispensing container while using the string, the user causes flossing compound to be dispensed, on the string during the flossing process.

The first flossing compound bearing cavity 42 and the second flossing compound bearing cavity 44 have specific shapes with (see FIG. 4) compound holding portions adapted to hold, mainly be surface attraction, predetermined quantities of flossing compound. As seen, each also has a metering portion connecting the associated holding portion to the surface of the taut string of dental floss. Such metering portions or simply reduced size openings which regulate the flow of flossing compound towards the surface of the taut string of dental floss to provide a steady supply of flossing compound during the flossing process under the urge of the inertial forces interacting with the vibrating motion of the arm ends 36 and 37. The composition of the flossing compound comprises components useful to dental hygiene and additives to provide the desired consistency and adequate flow under the conditions present during flossing.

Figure 5:
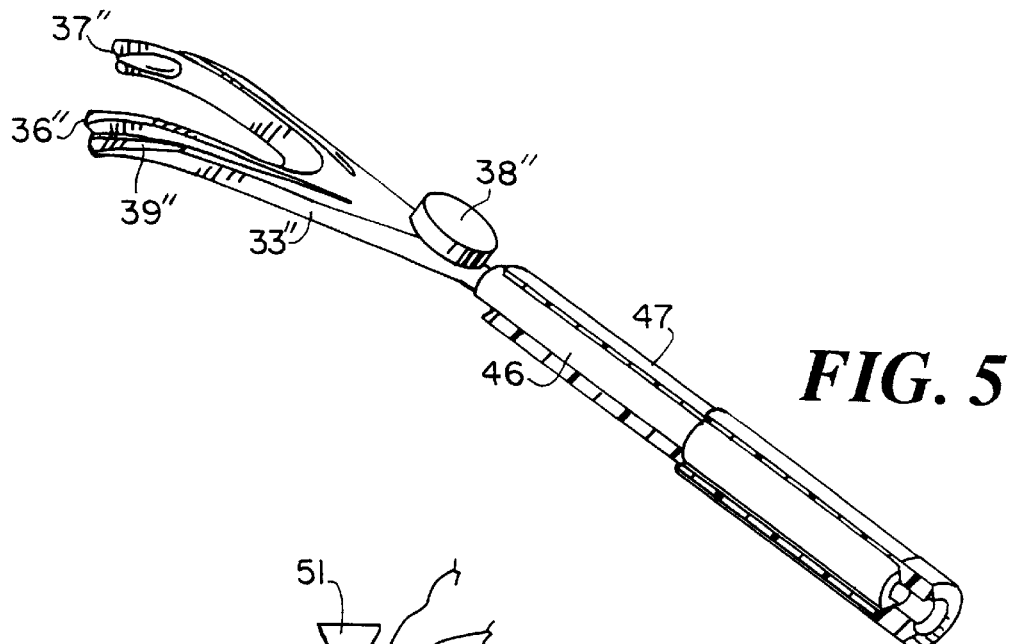
FIG. 5 is an isometric view of a second embodiment of the invention.

Another embodiment of the invention is illustrated in FIG. 5. In many ways this embodiment is similar to the earlier described embodiment and like parts are referred to by the same reference numerals, primed. This embodiment differs from the earlier described embodiment primarily in the way in which it is driven. As illustrated, it has a drive 46 designed for interaction with a drive component of another type of power-driven toothbrush (not shown). This embodiment is provided with a cover 47 for separating the drive from a user and thus protecting him/her during use of the device. In this connection, the cover is kept stationary relative to the moving drive during operation.

Figure 6:
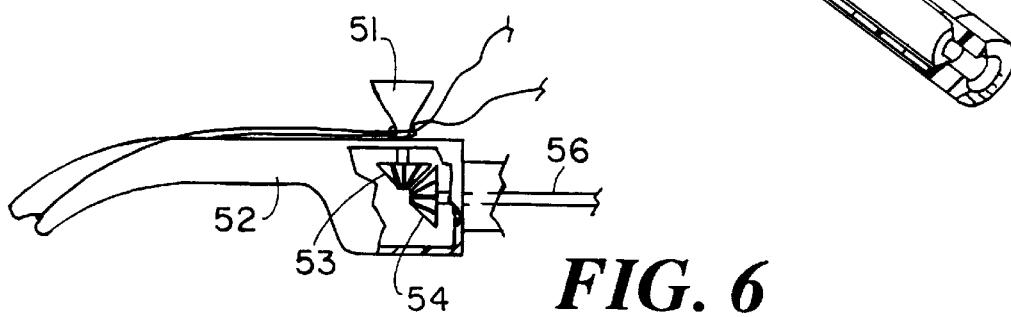
FIG. 6 is a broken away schematic depicting a third embodiment of the invention.

It is to be noted that in both this embodiment and the earlier described embodiment the movement which is transmitted to the yoke and, hence, the floss string is vibratory movement. FIG. 6 shows another embodiment of the invention in which the movement is continuous rotation. In such arrangement, the tie-in post 51 of such embodiment is rotatably mounted on a yoke 52 having a hollow (at least partially) interior, which post projects into the yoke interior and terminates in a beveled gear 53. Such beveled gear 53 is engaged by a corresponding beveled gear 54 on the end of a drive shaft 56. Such drive shaft is not shown in detail since the manner of its connection to a continuously rotating drive component of a toothbrush handle assembly will be quite obvious to one skilled in the art.

It should be noted that while this embodiment as illustrated provides continuous rotation, it would be easy for one to provide oscillating rotation simply by oscillating drive shaft 56 rather than rotating the same.

This embodiment having the moving floss post is particularly adaptable for use with a continuous loop a of predetermined length of floss string. Such a loop provides user comfort and enhanced usefulness. The user can conveniently slide the loop over the loop holding post and the two loop holding tips and proceed with flossing. The floss will not be able to become loose during the flossing process and the user will not have to worry about tying the floss under tension.

Figure 7:
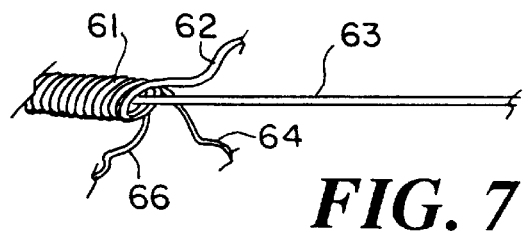
FIG. 7 is an enlarged showing of floss string structure of the invention.

The invention is particularly applicable to the use of effervescent action. FIG. 7 illustrates a floss string arrangement that is especially designed for use with the converter of the invention. As shown, the floss string 61 of FIG. 7 is made up of a plurality of filaments 62, 63, 64, and 66. At least one of these filaments is of a structurally sound material like, for example, nylon, silk or a similar man made or natural fiber. The surface of such filament is coated with a chemically active component. Examples of such chemically active components include: acidic substances (like, for example, citric acid, acetic acid, dried lemon juice, vinegar), metallic deposits (like, for example, platinum, titanium, or stanium), metallic salts (salts of, for example, iron, copper, chromium, vanadium, tungsten, molybdenum and platinum). This chemically active component is a necessary ingredient to effervescent reaction provided by the flossing compound discussed previously. The result is that the effervescent reaction is only initiated at the interface between the component and the flossing compounds.

A further enhancement is provided by covering the chemically active filament, say filament 63, with one or more structural filaments that do not contain any chemically active agent on their surface. The chemically inert "cover" provided by the other filaments will prevent, by mechanical interference, the normally viscous flossing compound from coming into contact prematurely with the chemically active part of the floss string. Good contact between the flossing compound and the chemically active part of the floss string will thus be limited to the zone of vigorous mechanical activity in the immediate vicinity of the point of contact between the tooth surface and the floss string. The effervescent reaction will therefore be most active at the contact point between the floss and the tooth where it aids tooth cleaning most effectively.

The flossing compound most desirably will contain a component chosen to react with the chemically active component of the flossing string and release a gas. Examples of such components include sodium bicarbonate, potassium bicarbonate, peroxide, potassium nitrite, etc.

Figure 8:
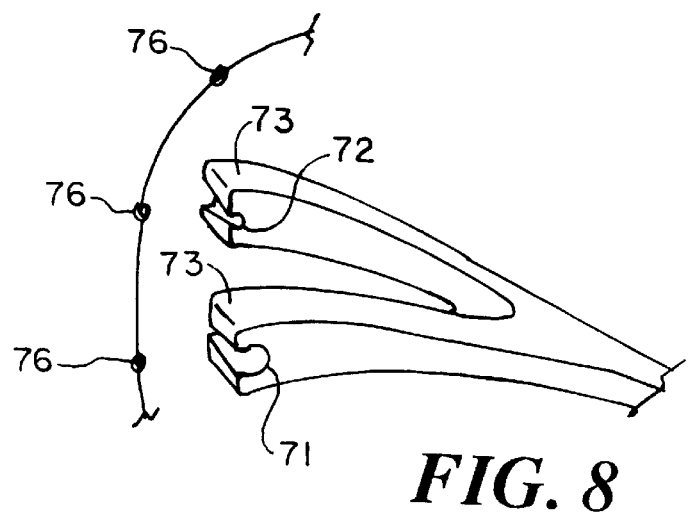
FIG. 8 is an enlarged partial isometric showing an alternate configuration for the invention.

FIG. 8 shows another approach to solving the need for easy flosser setup and adequate flossing string tension during use. The arrangement illustrated is configured with conical apertures 71 and 72 at the floss holding tips 73 of the floss holding fork. These conical apertures have their larger side towards the exterior of the floss holding fork. The user is provided with a string of dental floss 74 that has at least two beads 76 attached to the floss string, such beads being a predetermined distance from each other that is slightly less than the distance between the floss holding tips of the fork arms. The user inserts a first bead into a first orifice, presses the two floss holding arms of the floss holding fork slightly towards each other, slides the second bead into the second orifice of the fork, releases the pressure from the floss holding arm such that the floss holding arms urge the two beads attached to the flossing string away from each other and thus force the string of floss to stretch taut under the urging of the beads. The flosser with the flossing string so mounted can then be used to floss one's teeth. The floss string can be made available to the user wound up in rolls of string containing beads which are predetermined distances from one another.

As mentioned at the beginning of the detailed description, applicant is not limited to the specific embodiment and variations described above. They are exemplary, rather than exhaustive. The claims, their equivalents and their equivalent language define the scope of protection.

What is claimed is:

1. A tooth flossing device for dental hygiene, which device is designed to use an existing electric power-driven toothbrush to itself become a power-driven flossing device in which floss string is moved, comprising:

A. means for receiving energy from said toothbrush originally provided to move toothbrush bristles; and B. means for converting received energy into movement of a floss string for dental hygiene instead of movement of toothbrush bristles, which converting means includes a yoke having a pair of arms which project away from one another to define separated free arm ends between which a floss string can be provided, each of said free arm ends being configured to interact with an associated anomaly provided in a floss string for the purpose of preventing floss string at the location of such anomaly from moving toward the other of said arms, said means for receiving energy including means for moving said floss string relative to said free arm ends.

2. A tooth flossing device for dental hygiene, which device is designed to use an existing electric power-driven toothbrush to itself become a power-driven flossing device in which floss string is moved, comprising:

A. means for receiving energy from said toothbrush originally provided to move toothbrush bristles; and B. means for converting received energy into movement of a floss string for dental hygiene instead of movement of toothbrush bristles, which converting means includes a yoke having a pair of arms which project from one another to define separated free arm ends for holding floss string therebetween, each of said arms having an interior side facing the other side arm, and at least one of said interior sides having a cavity configured to hold a flowable floss compound on the interior side of at least one of said free arm ends to enable a flowable floss compound to be used for dental hygiene along with said floss string.

3. The tooth flossing device of claim 2 wherein said cavity includes both a compound holding portion and a metering portion to regulate the flow of the compound from said holding portion towards a floss string at said free arm end.

4. The tooth flossing device of claim 2 wherein there is a cavity for a flowable flossing compound in the interior side of both of said arms adjacent the free end of the associated arm.

5. A tooth flossing device comprising:

A. a yoke having a pair of arms which project away from one another to define separated free arm ends between which a floss string can be provided; and B. a cavity configured to hold a flowable floss compound defined by at least one of said free arm ends to enable a flowable floss compound to be provided along with said floss string for dental hygiene.

6. A tooth flossing device of claim 5 wherein said cavity includes both a compound holding portion and a metering portion to regulate the flow of the compound from said holding portion towards a floss string at said free arm end.

* * * * *